`US012006274B2`

United States Patent
Sun et al.

(10) Patent No.: US 12,006,274 B2
(45) Date of Patent: *Jun. 11, 2024

(54) COMPOSITIONS INCLUDING OLEFIN AND HYDROFLUOROALKANE

(71) Applicant: THE CHEMOURS COMPANY FC, LLC, Wilmington, DE (US)

(72) Inventors: Xuehui Sun, Kennett Square, PA (US); Mario Joseph Nappa, Leesburg, FL (US); Karl Krause, Kennett Square, PA (US)

(73) Assignee: The Chemours Company FC, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,391

(22) Filed: Nov. 3, 2022

(65) Prior Publication Data

US 2023/0075222 A1    Mar. 9, 2023

Related U.S. Application Data

(60) Continuation of application No. 17/656,340, filed on Mar. 24, 2022, which is a division of application No. 17/220,427, filed on Apr. 1, 2021, now Pat. No. 11,572,326, which is a division of application No. 16/423,352, filed on May 28, 2019, now Pat. No. 11,008,267, which is a continuation of application No. 15/575,526, filed as application No. PCT/US2016/033450 on May 20, 2016, now Pat. No. 10,301,236.

(60) Provisional application No. 62/164,631, filed on May 21, 2015.

(51) Int. Cl.
| | | |
|---|---|---|
| C07C 21/18 | (2006.01) | |
| B01J 23/16 | (2006.01) | |
| B01J 23/18 | (2006.01) | |
| B01J 27/08 | (2006.01) | |
| C07C 17/08 | (2006.01) | |
| C07C 17/087 | (2006.01) | |
| C07C 17/20 | (2006.01) | |
| C07C 17/25 | (2006.01) | |
| C07C 19/08 | (2006.01) | |
| C07C 19/10 | (2006.01) | |

(52) U.S. Cl.
CPC ............ *C07C 17/087* (2013.01); *B01J 23/16* (2013.01); *B01J 23/18* (2013.01); *B01J 27/08* (2013.01); *C07C 17/08* (2013.01); *C07C 17/206* (2013.01); *C07C 17/25* (2013.01); *C07C 19/08* (2013.01); *C07C 19/10* (2013.01); *C07C 2527/12* (2013.01); *C07C 2527/133* (2013.01)

(58) Field of Classification Search
None
See application file for complete search history.

(56) References Cited

U.S. PATENT DOCUMENTS

| | | | |
|---|---|---|---|
| 5,155,082 A | 10/1992 | Tung et al. | |
| 5,446,217 A * | 8/1995 | Van Der Puy | .......... C07C 21/18 570/135 |
| 5,689,019 A | 11/1997 | Aoyama et al. | |
| 7,795,480 B2 | 9/2010 | Merkel et al. | |
| 7,803,283 B2 | 9/2010 | Pham et al. | |
| 7,829,748 B1 | 11/2010 | Tung | |
| 8,034,251 B2 | 10/2011 | Merkel et al. | |
| 8,058,486 B2 | 11/2011 | Merkel et al. | |
| 8,067,649 B2 | 11/2011 | Kopkalli et al. | |
| 8,070,975 B2 | 12/2011 | Pham et al. | |
| 8,071,825 B2 | 12/2011 | Johnson et al. | |
| 8,076,521 B2 | 12/2011 | Elsheikh et al. | |
| 8,114,308 B2 | 2/2012 | Merkel et al. | |
| 8,119,845 B2 | 2/2012 | Merkel et al. | |
| 8,168,837 B2 | 5/2012 | Merkel et al. | |
| 8,203,022 B2 | 6/2012 | Nappa | |
| 8,252,964 B2 | 8/2012 | Devic et al. | |
| 8,252,965 B2 | 8/2012 | Merkel et al. | |
| 8,314,159 B2 | 11/2012 | Chen et al. | |
| 8,344,191 B2 | 1/2013 | Nose et al. | |
| 8,367,878 B2 | 2/2013 | Merkel et al. | |
| 8,426,658 B2 | 4/2013 | Pham et al. | |
| 8,445,735 B2 | 5/2013 | Nappa | |
| 8,454,853 B2 | 6/2013 | Van Horn et al. | |
| 8,455,704 B2 | 6/2013 | Johnson et al. | |
| 8,481,793 B2 | 7/2013 | Merkel et al. | |
| 8,519,201 B2 | 8/2013 | Merkel et al. | |
| 8,546,624 B2 | 10/2013 | Pham et al. | |
| 8,563,789 B2 | 10/2013 | Elsheikh et al. | |

(Continued)

FOREIGN PATENT DOCUMENTS

| | | |
|---|---|---|
| AU | 2010341533 A1 | 6/2012 |
| BR | 112012015260 A2 | 4/2017 |

(Continued)

OTHER PUBLICATIONS

Cn104140354a, machine translation, pp. 1-5, Dec. 12, 2014 (Year: 2014).*

(Continued)

*Primary Examiner* — Medhanit W Bahta
(74) *Attorney, Agent, or Firm* — McNees Wallace & Nurick LLC

(57) ABSTRACT

A method hydrofluorinates an olefin of the formula: RCX=CYZ to produce a hydrofluoroalkane of formula RCXFCHYZ or RCXHCFYZ, where X, Y, and Z are independently the same or different and are selected from the group consisting of H, F, Cl, Br, and $C_1$-$C_6$ alkyl which is partially or fully substituted with chloro or fluoro or bromo; and R is a $C_1$-$C_6$ alkyl which is unsubstituted or substituted with chloro or fluoro or bromo. The method includes reacting the olefin with HF in the vapor phase, in the presence of $SbF_5$, at a temperature ranging from about −30° C. to about 65° C. and compositions formed by the process.

20 Claims, No Drawings

(56) References Cited

U.S. PATENT DOCUMENTS

| | | |
|---|---|---|
| 8,618,338 B2 | 12/2013 | Elsheikh et al. |
| 8,618,340 B2 | 12/2013 | Kopkalli et al. |
| 8,648,123 B2 | 2/2014 | Van Horn et al. |
| 8,664,455 B2 | 3/2014 | Merkel et al. |
| 8,680,345 B2 | 3/2014 | Merkel et al. |
| 8,697,922 B2 | 4/2014 | Nappa |
| 8,716,538 B2 | 5/2014 | Merkel et al. |
| 8,741,828 B2 | 6/2014 | Hulse et al. |
| 8,754,271 B2 | 6/2014 | Mukhopadhyay et al. |
| 8,772,364 B2 | 7/2014 | Van Horn et al. |
| 8,772,554 B2 | 7/2014 | Nose et al. |
| 8,796,493 B2 | 8/2014 | Merkel et al. |
| 8,835,698 B2 | 9/2014 | Johnson et al. |
| 8,845,921 B2 | 9/2014 | Merkel et al. |
| 8,846,990 B2 | 9/2014 | Wang et al. |
| 8,859,829 B2 | 10/2014 | Kopkalli et al. |
| 2007/0197842 A1 | 8/2007 | Mukhopadhyay et al. |
| 2008/0157022 A1 | 7/2008 | Singh et al. |
| 2009/0030244 A1 | 1/2009 | Merkel et al. |
| 2009/0030247 A1 | 1/2009 | Johnson et al. |
| 2009/0149680 A1 | 6/2009 | Wang |
| 2009/0182179 A1 | 7/2009 | Merkel et al. |
| 2009/0211988 A1 | 8/2009 | Pham et al. |
| 2009/0224207 A1 | 9/2009 | Pham et al. |
| 2009/0227822 A1 | 9/2009 | Pham et al. |
| 2009/0240090 A1 | 9/2009 | Merkel et al. |
| 2009/0242832 A1 | 10/2009 | Pham et al. |
| 2009/0256110 A1 | 10/2009 | Merkel et al. |
| 2009/0287026 A1 | 11/2009 | Kopkalli et al. |
| 2009/0287027 A1 | 11/2009 | Merkel et al. |
| 2010/0036179 A1 | 2/2010 | Merkel et al. |
| 2010/0048961 A1 | 2/2010 | Merkel et al. |
| 2010/0056657 A1 | 3/2010 | Chen et al. |
| 2010/0076100 A1 | 3/2010 | Chen |
| 2010/0087557 A1 | 4/2010 | Chen et al. |
| 2010/0105788 A1 | 4/2010 | Chen et al. |
| 2010/0105789 A1 | 4/2010 | Van Horn et al. |
| 2010/0105967 A1 | 4/2010 | Nappa |
| 2010/0112328 A1 | 5/2010 | Van Horn et al. |
| 2010/0113629 A1 | 5/2010 | Van Horn et al. |
| 2010/0154419 A1 | 6/2010 | Kontomaris |
| 2010/0185030 A1 | 7/2010 | Elsheikh et al. |
| 2010/0187088 A1 | 7/2010 | Merkel et al. |
| 2010/0331583 A1 | 12/2010 | Johnson et al. |
| 2011/0001080 A1 | 1/2011 | Van Horn et al. |
| 2011/0004035 A1 | 1/2011 | Merkel et al. |
| 2011/0012052 A1 | 1/2011 | Van Horn et al. |
| 2011/0031436 A1* | 2/2011 | Mahler ............... C07C 17/25 252/78.1 |
| 2011/0088418 A1 | 4/2011 | Kontomaris et al. |
| 2011/0105807 A1 | 5/2011 | Kopkalli et al. |
| 2011/0105809 A1 | 5/2011 | Devic et al. |
| 2011/0178344 A1 | 7/2011 | Nose et al. |
| 2011/0197602 A1 | 8/2011 | Abbas et al. |
| 2011/0201851 A1 | 8/2011 | Nose et al. |
| 2011/0207974 A9 | 8/2011 | Kopkalli et al. |
| 2011/0207975 A9 | 8/2011 | Merkel et al. |
| 2011/0210289 A9 | 9/2011 | Merkel et al. |
| 2011/0219811 A1 | 9/2011 | Kontomaris |
| 2011/0226004 A1 | 9/2011 | Kontomaris |
| 2011/0240902 A1 | 10/2011 | Merkel et al. |
| 2011/0245548 A1 | 10/2011 | Merkel et al. |
| 2011/0270000 A1 | 11/2011 | Bektesevic et al. |
| 2012/0037843 A1 | 2/2012 | Pham et al. |
| 2012/0043492 A1 | 2/2012 | Williams et al. |
| 2012/0053371 A1 | 3/2012 | Johnson et al. |
| 2012/0059202 A1 | 3/2012 | Elsheik et al. |
| 2012/0065437 A1 | 3/2012 | Merkel et al. |
| 2012/0078020 A1 | 3/2012 | Elsheik et al. |
| 2012/0101177 A1 | 4/2012 | Van Horn et al. |
| 2012/0108688 A1 | 5/2012 | Van Horn et al. |
| 2012/0136182 A1 | 5/2012 | Merkel et al. |
| 2012/0178977 A1 | 7/2012 | Merkel et al. |
| 2012/0187330 A1 | 7/2012 | Singh et al. |
| 2012/0190901 A1 | 7/2012 | Merkel et al. |
| 2012/0202904 A1 | 8/2012 | Chen et al. |
| 2012/0215035 A1 | 8/2012 | Nappa |
| 2012/0215036 A1 | 8/2012 | Sun et al. |
| 2012/0215037 A1 | 8/2012 | Sun et al. |
| 2012/0215038 A1 | 8/2012 | Sun et al. |
| 2012/0215039 A1 | 8/2012 | Hulse et al. |
| 2012/0216551 A1 | 8/2012 | Minor et al. |
| 2012/0222448 A1 | 9/2012 | Chaki et al. |
| 2012/0225961 A1 | 9/2012 | Van Horn et al. |
| 2012/0232316 A1 | 9/2012 | Nappa |
| 2012/0232317 A1 | 9/2012 | Nappa |
| 2012/0240477 A1 | 9/2012 | Nappa |
| 2012/0272668 A1 | 11/2012 | Van Horn et al. |
| 2012/0292556 A1 | 11/2012 | Van Horn |
| 2012/0296128 A1 | 11/2012 | Merkel et al. |
| 2012/0304682 A1 | 12/2012 | Kontomaris |
| 2012/0304686 A1 | 12/2012 | Kontomaris |
| 2013/0035410 A1 | 2/2013 | Chen et al. |
| 2013/0035526 A1 | 2/2013 | Elsheik et al. |
| 2013/0041048 A1 | 2/2013 | Chen et al. |
| 2013/0085308 A1 | 4/2013 | Merkel et al. |
| 2013/0096218 A1 | 4/2013 | Rached et al. |
| 2013/0099154 A1 | 4/2013 | Boussand et al. |
| 2013/0105296 A1 | 5/2013 | Chaki et al. |
| 2013/0119300 A1 | 5/2013 | Van Horn et al. |
| 2013/0158305 A1 | 6/2013 | Takahashi |
| 2013/0197282 A1 | 8/2013 | Merkel et al. |
| 2013/0217928 A1 | 8/2013 | Takahashi et al. |
| 2013/0246288 A1 | 9/2013 | Van Horn et al. |
| 2013/0253235 A1 | 9/2013 | Johnson et al. |
| 2013/0281557 A1 | 10/2013 | Van Horn et al. |
| 2013/0338408 A1 | 12/2013 | Merkel et al. |
| 2014/0005288 A1 | 1/2014 | Chen et al. |
| 2014/0012047 A1 | 1/2014 | Merkel et al. |
| 2014/0012048 A9 | 1/2014 | Sun et al. |
| 2014/0012051 A1 | 1/2014 | Pigamo et al. |
| 2014/0012052 A1 | 1/2014 | Pham et al. |
| 2014/0018582 A1 | 1/2014 | Sun et al. |
| 2014/0031442 A1 | 1/2014 | Van Horn et al. |
| 2014/0039228 A1 | 2/2014 | Pigamo et al. |
| 2014/0051776 A1 | 2/2014 | Chen et al. |
| 2014/0070129 A1 | 3/2014 | Kennoy et al. |
| 2014/0100393 A9 | 4/2014 | Johnson et al. |
| 2014/0103248 A1 | 4/2014 | Van Horn et al. |
| 2014/0121424 A1 | 5/2014 | Nose et al. |
| 2014/0147343 A1 | 5/2014 | Merkel et al. |
| 2014/0194656 A1 | 7/2014 | Chaki et al. |
| 2014/0213677 A1 | 7/2014 | Jimenez et al. |
| 2014/0213678 A1 | 7/2014 | Van Horn et al. |
| 2014/0235903 A1 | 8/2014 | Wang et al. |
| 2014/0235904 A1 | 8/2014 | Bektesevic et al. |
| 2014/0249336 A1 | 9/2014 | Komatsu et al. |
| 2014/0256995 A1 | 9/2014 | Wang et al. |
| 2014/0256996 A1 | 9/2014 | Wang et al. |
| 2014/0275646 A1 | 9/2014 | Wang et al. |
| 2014/0275648 A1 | 9/2014 | Chiu |
| 2014/0275649 A1 | 9/2014 | Wang et al. |
| 2014/0275650 A1 | 9/2014 | Kopkalli et al. |
| 2014/0275651 A1 | 9/2014 | Wang et al. |
| 2014/0275652 A1 | 9/2014 | Wang et al. |
| 2014/0275653 A1 | 9/2014 | Pigamo et al. |
| 2014/0275655 A1 | 9/2014 | Wang et al. |
| 2014/0296360 A1 | 10/2014 | Chen et al. |
| 2014/0296585 A1 | 10/2014 | Deur-Bert et al. |
| 2014/0303409 A1 | 10/2014 | Wang et al. |
| 2014/0303412 A1 | 10/2014 | Karube et al. |
| 2014/0303413 A1 | 10/2014 | Merkel et al. |
| 2014/0309462 A1 | 10/2014 | Nappa et al. |
| 2014/0309463 A1 | 10/2014 | Bektesevic et al. |
| 2015/0241095 A1 | 8/2015 | Nappa |
| 2015/0247674 A1 | 9/2015 | Nappa |
| 2015/0247675 A1 | 9/2015 | Nappa |
| 2015/0251033 A1 | 9/2015 | Nappa |

(56) References Cited

U.S. PATENT DOCUMENTS

| | | | |
|---|---|---|---|
| 2018/0208528 A1 | 7/2018 | Giddis et al. | |
| 2018/0214727 A1 | 8/2018 | Nappa | |

FOREIGN PATENT DOCUMENTS

| | | |
|---|---|---|
| CA | 2782592 A1 | 7/2011 |
| CA | 3016991 A1 | 7/2011 |
| CA | 3017000 A1 | 7/2011 |
| CN | 102686694 A | 9/2012 |
| CN | 104140354 A | 11/2014 |
| CN | 104140355 A | 11/2014 |
| CN | 105062427 A | 11/2015 |
| EP | 2 096 096 A1 | 9/2009 |
| EP | 2 098 499 A1 | 9/2009 |
| EP | 2 103 587 A2 | 9/2009 |
| EP | 2 107 048 A1 | 10/2009 |
| EP | 2 108 638 A1 | 10/2009 |
| EP | 2 119 692 A1 | 11/2009 |
| EP | 2 151 425 A2 | 2/2010 |
| EP | 2 157 073 A1 | 2/2010 |
| EP | 2 258 789 A2 | 12/2010 |
| EP | 2 287 271 A2 | 2/2011 |
| EP | 2 412 753 A1 | 2/2012 |
| EP | 2 516 577 A1 | 10/2012 |
| EP | 2 583 959 A1 | 4/2013 |
| EP | 2 615 079 A1 | 7/2013 |
| EP | 2 634 165 A2 | 9/2013 |
| EP | 2 634 166 A2 | 9/2013 |
| EP | 2 634 231 A2 | 9/2013 |
| EP | 2 634 232 A2 | 9/2013 |
| EP | 2 690 129 A2 | 1/2014 |
| EP | 2 756 883 A2 | 7/2014 |
| EP | 2 845 891 A2 | 3/2015 |
| JP | H0824362 A | 1/1996 |
| JP | H08193039 A | 7/1996 |
| JP | H10251172 A | 9/1998 |
| JP | 2009167187 A | 7/2009 |
| JP | 2010043080 A | 2/2010 |
| JP | 2010215622 A | 9/2010 |
| JP | 2013515158 A | 5/2013 |
| JP | 2018031013 A | 3/2018 |
| JP | 2018141159 A | 9/2019 |
| KR | 20120123355 A | 11/2012 |
| KR | 20180011354 A | 1/2018 |
| MX | 351915 B | 11/2017 |
| MX | 356473 B | 5/2018 |
| MY | 159904 A | 2/2017 |
| RU | 2012131170 A | 1/2014 |
| SG | 181873 A1 | 1/2014 |
| SG | 10201509239X | 12/2015 |
| WO | 2006/069362 A2 | 6/2006 |
| WO | 2008/121776 A1 | 10/2008 |
| WO | 2008/121778 A1 | 10/2008 |
| WO | 2008/121779 A1 | 10/2008 |
| WO | 2008/121783 A1 | 10/2008 |
| WO | 2008/121785 A1 | 10/2008 |
| WO | 2008/121787 A1 | 10/2008 |
| WO | 2008/121790 A1 | 10/2008 |
| WO | 2009/003084 A1 | 12/2008 |
| WO | 2009/015317 A1 | 1/2009 |
| WO | 2009/018561 A2 | 2/2009 |
| WO | 2009/114397 A2 | 9/2009 |
| WO | 2009/137658 A2 | 11/2009 |
| WO | 2009/140563 A1 | 11/2009 |
| WO | 2009/148191 A1 | 12/2009 |
| WO | 2009/151669 A1 | 12/2009 |
| WO | 2010/001025 A2 | 1/2010 |
| WO | 2010/013795 A1 | 2/2010 |
| WO | 2010/013796 A1 | 2/2010 |
| WO | 2010/062527 A1 | 6/2010 |
| WO | 2010/062888 A2 | 6/2010 |
| WO | 2010/080467 A2 | 7/2010 |
| WO | 2011/031598 A1 | 3/2011 |
| WO | 2011/038081 A1 | 3/2011 |
| WO | 2011/050017 A1 | 4/2011 |
| WO | 2011/056441 A2 | 5/2011 |
| WO | 2011/056824 A2 | 5/2011 |
| WO | 2011/059078 A1 | 5/2011 |
| WO | 2011/082003 A1 | 7/2011 |
| WO | 2011/087825 A1 | 7/2011 |
| WO | 2011/091404 A1 | 7/2011 |
| WO | 2011/126620 A2 | 10/2011 |
| WO | 2011/126634 A2 | 10/2011 |
| WO | 2011/126679 A2 | 10/2011 |
| WO | 2011/130108 A1 | 10/2011 |
| WO | 2011/137033 A1 | 11/2011 |
| WO | 2011/139646 A2 | 11/2011 |
| WO | 2012/006206 A2 | 1/2012 |
| WO | 2012/009114 A2 | 1/2012 |
| WO | 2012/011609 A1 | 1/2012 |
| WO | 2012/024252 A2 | 2/2012 |
| WO | 2012/033088 A1 | 3/2012 |
| WO | 2012/057367 A1 | 5/2012 |
| WO | 2012/067980 A2 | 5/2012 |
| WO | 2012/087667 A1 | 6/2012 |
| WO | 2012/09447 A2 | 7/2012 |
| WO | 2012/098421 A1 | 7/2012 |
| WO | 2012/098422 A1 | 7/2012 |
| WO | 2012/115930 A1 | 8/2012 |
| WO | 2012/115934 A1 | 8/2012 |
| WO | 2012/115938 A1 | 8/2012 |
| WO | 2012/115957 A1 | 8/2012 |
| WO | 2012/121876 A2 | 9/2012 |
| WO | 2012/141822 A1 | 10/2012 |
| WO | 2012/158870 A1 | 11/2012 |
| WO | 2012/173273 A1 | 12/2012 |
| WO | 2013/007906 A1 | 1/2013 |
| WO | 2013/015068 A1 | 1/2013 |
| WO | 2013/037286 A1 | 3/2013 |
| WO | 2013/0139260 A2 | 3/2013 |
| WO | 2013/045791 A1 | 4/2013 |
| WO | 2013/049105 A1 | 4/2013 |
| WO | 2013/049742 A1 | 4/2013 |
| WO | 2013/049743 A1 | 4/2013 |
| WO | 2013/049744 A2 | 4/2013 |
| WO | 2013/053555 A2 | 4/2013 |
| WO | 2013/055722 A1 | 4/2013 |
| WO | 2013/055726 A1 | 4/2013 |
| WO | 2013/055894 A1 | 4/2013 |
| WO | 2013/065617 A1 | 5/2013 |
| WO | 2013/067350 A1 | 5/2013 |
| WO | 2013/067356 A1 | 5/2013 |
| WO | 2013/071024 A1 | 5/2013 |
| WO | 2013/074324 A1 | 5/2013 |
| WO | 2013/088195 A1 | 6/2013 |
| WO | 2013/093272 A1 | 6/2013 |
| WO | 2013/106305 A1 | 7/2013 |
| WO | 2013/111911 A1 | 8/2013 |
| WO | 2013/114015 A1 | 8/2013 |
| WO | 2013/116416 A1 | 8/2013 |
| WO | 2013/119919 A1 | 8/2013 |
| WO | 2013/130385 A1 | 9/2013 |
| WO | 2013/138123 A1 | 9/2013 |
| WO | 2013/174844 A1 | 11/2013 |
| WO | 2013/182816 A1 | 12/2013 |
| WO | 2013/182818 A1 | 12/2013 |
| WO | 2013/184865 A1 | 12/2013 |
| WO | 2014/010750 A1 | 1/2014 |
| WO | 2014/015315 A1 | 1/2014 |
| WO | 2014/022610 A1 | 2/2014 |
| WO | 2014/025065 A1 | 2/2014 |
| WO | 2014/028574 A2 | 2/2014 |
| WO | 2014/047230 A1 | 3/2014 |
| WO | 2014/102479 A1 | 7/2014 |
| WO | 2014/147310 A1 | 9/2014 |
| WO | 2014/147311 A1 | 9/2014 |
| WO | 2014/147312 A1 | 9/2014 |
| WO | 2014/147313 A1 | 9/2014 |
| WO | 2014/147314 A1 | 9/2014 |
| WO | 2014/150889 A1 | 9/2014 |
| WO | 2014/151270 A1 | 9/2014 |
| WO | 2014/151441 A1 | 9/2014 |
| WO | 2014/151448 A1 | 9/2014 |
| WO | 2014/152325 A1 | 9/2014 |

(56) References Cited

FOREIGN PATENT DOCUMENTS

WO  2014/159809 A1  10/2014
WO  2014/159818 A1  10/2014
WO  2014/164611 A1  10/2014

OTHER PUBLICATIONS

English Translation of JP Office Action, JP Application No. 2017-560782, dated Mar. 9, 2020.
European Examination Report for EP Application No. 16797362.7, dated May 27, 2020, 3 pages.
International Search Report dated Aug. 22, 2016 issued in PCT/US2016/033450.
Teinz et al., "Catalytic formulation of 2,3,3,3-tetrafluoropropene from 2-chloro-3,3,3-trifluoropropene at fluorinated chromia: A study of reaction pathways", Applied Catalysis B: Environmental, vol. 165, pp. 200-208 (2015).

* cited by examiner

COMPOSITIONS INCLUDING OLEFIN AND HYDROFLUOROALKANE

CROSS-REFERENCE TO RELATED APPLICATIONS

This application is a continuation of co-pending U.S. application Ser. No. 17/656,340 filed Mar. 24, 2022, which is a divisional of co-pending U.S. application Ser. No. 17/220,427 filed Apr. 1, 2021, which is a divisional of U.S. application Ser. No. 16/423,352 filed May 28, 2019, now U.S. Pat. No. 11,008,267, which is a continuation of U.S. application Ser. No. 15/575,526 filed Nov. 20, 2017, now U.S. Pat. No. 10,301,236, which is a 371 National Stage Application of PCT/US2016/033450 filed May 20, 2016, which claims the benefit of and priority to U.S. Provisional Application No. 62/164,631 filed May 21, 2015, all of which are hereby incorporated by reference in their entirety.

BACKGROUND OF THE INVENTION

This disclosure relates to novel methods for preparing fluorinated organic compounds, and more particularly to methods of producing fluorinated hydrocarbons.

Hydrofluorocarbons (HFCs), in particular hydrofluoroalkenes or fluoroolefins, such as tetrafluoropropenes (including 2,3,3,3-tetrafluoro-1-propene (HFO-1234yf or 1234yf)) have been disclosed to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and, thus, pose no threat to the ozone layer.

In addition to ozone depleting concerns, global warming is another environmental concern in many of these applications. Thus, there is a need for compositions that meet both low ozone depletion standards as well as having low global warming potentials. Certain fluoroolefins are believed to meet both goals. Thus, there is a need for manufacturing processes that provide halogenated hydrocarbons and fluoroolefins that contain no chlorine that also have a low global warming potential.

One such HFO is 2,3,3,3-tetrafluoro-1-propene (HFO-1234yf or 1234yf). The preparation of HFO-1234yf starting from $CQ_2=CCl-CH_2Q$ or $CQ_3-CCl=CH_2$ or $CQ_3-CHCl-CH_2Q$ may include three reaction steps, as follows:
  (i) ($CQ_2=CCl-CH_2Q$ or $CQ_3-CCl=CH_2$ or $CQ_3-CHCl-CH_2Q$)+HF-2-chloro-3,3,3-trifluoropropene (HCFO-1233xf or 1233xf)+HCl in a vapor phase reactor charged with a solid catalyst;
  (ii) 2-chloro-3,3,3-trifluoropropene (HCFO-1233xf)+HF-2-chloro-1,1,1,2-tetrafluoropropane (HCFC-244bb or 244bb) in a liquid phase reactor charged with a liquid hydrofluorination catalyst; and
  (iii) 2-chloro-1,1,1,2-tetrafluoropropane (HCFC-244bb)-2,3,3,3-tetrafluoropropene (HFO-1234yf) in a vapor phase reactor;
  wherein Q is independently selected from F, Cl, Br, and I, provided that at least one Q is not fluorine.

The hydrofluorination of 1233xf to 244bb is usually conducted in the presence of fluorinated $SbCl_5$ at temperatures above 70° C.; otherwise the catalyst will freeze. Under these conditions, the 1233xf is not completely converted to 244bb because of equilibrium limitations, especially at higher temperatures. As a result, significant amounts of 1233xf are present in the product formed. Since the boiling points of 1233xf and 244bb are only about 2° C. apart, separation of these two species is difficult and expensive.

Moreover, the presence of 2-chloro-3,3,3-trifluoropropene (HCFO-1233xf) in the reaction starting materials, such as HCFC-244bb feedstock, can lead to dramatically reduced conversion of HCFC-244bb to HFO-1234yf. In addition, the 2-chloro-3,3,3-trifluoropropene copresence in the starting material, when subjected to dehydrochlorination, can lead to the formation of trifluoropropyne and oligomers, which can produce tar. This result is disadvantageous from the standpoint of a reduced yield of the desired product. Therefore, there is a need for a better catalytic reaction to achieve a higher conversion of 1233xf to 244bb to avoid and/or minimize the need for purification.

The present invention fulfills that need.

SUMMARY OF THE INVENTION

The disclosure relates to a method for hydrofluorination of an olefin of the formula: $RCX=CYZ$ to produce hydrofluoroalkanes of formula $RCXFCHYZ$ and $RCHXCFYZ$, wherein X, Y and Z are independently the same or different and are selected from the group consisting of H, F, Cl, Br, and $C_1$-$C_6$ alkyl which is partly or fully substituted with chloro or fluoro or bromo, and R is a $C_1$-$C_6$ alkyl which is partially or fully substituted with chloro or fluoro or bromo, comprising reacting the fluoroolefin with HF in the liquid-phase, in the presence of $SbF_5$, at a temperature ranging from about −30° C. to about 65° C.

DETAILED DESCRIPTION OF THE INVENTION

The foregoing general description and the following detailed description are exemplary and explanatory only and are not restrictive of the invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B is true (or present).

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

The term "olefin", as used herein refers to a compound containing a carbon-carbon double bond. It is defined herein relative to the formula $RCX=CYZ$.

The terms "hydrofluoroalkene" or "fluoroolefin", as used herein, denotes a compound containing hydrogen, carbon, fluorine, and at least one carbon-carbon double bond and optionally chlorine.

"HFO", as used herein, indicates a compound containing hydrogen, carbon, fluorine, and at least one carbon-carbon double, and no chlorine. "HCFO", as used herein, indicates a compound containing hydrogen, carbon, chlorine, fluorine, and at least one carbon-carbon double. "HCO", as used herein, indicates a compound containing hydrogen, carbon, chlorine, and at least one carbon-carbon double bond, and no fluorine.

The term "hydrofluorination" is understood to mean the addition reaction of hydrogen fluoride to a carbon-carbon double bond.

The term "hydrofluoroalkane", as used herein, refers to an alkane having two or more carbon atoms containing hydrogen, fluorine, and optionally chlorine, whereby a fluorine atom and a hydrogen atom are substituted on two adjacent carbon atoms. As used herein, the hydrofluoroalkane can be the product from the hydrofluorination of the fluoroolefin.

The HF used herein is an anhydrous liquid hydrogen fluoride which is commercially available or it may be a gas that is bubbled into the reactor. Anhydrous HF is sold by, for example, Solvay S. A, The Chemours Company FC, LLC and Honeywell International, Inc.

As used herein, the term "conversion" with respect to a reactant, which typically is a limiting agent, refers to the number of moles reacted in the reaction process divided by the number of moles of that reactant initially present in the process multiplied by 100.

As used herein, percent conversion is defined as 100%, less the weight percent of starting material in the effluent from the reaction vessel.

As used herein, the term "selectivity" with respect to an organic reaction product refers to the ratio of the moles of that reaction product to the total of the moles of the organic reaction products multiplied by 100.

As used herein, "percent selectivity" is defined as the weight of a desired product formed, as a fraction of the total amount of the products formed in the reaction, and excluding the starting material.

Some fluoroolefins of this disclosure, e.g., $CF_3CH=CHCl$ (HCFO-1233zd or 1233zd), exist as different configurational isomers or stereoisomers. When the specific isomer is not designated, the present disclosure is intended to include all single configurational isomers, single stereoisomers, or any combination thereof. For instance, HCFO-1233zd is meant to represent the E-isomer, Z-isomer, or any combination or mixture of both isomers in any ratio.

Described is a method for producing hydrofluoroalkanes of formula RCXFCHYZ, wherein X, Y and Z may independently be the same or different and are selected from H, F, Cl and an alkyl group having 1 to 6 carbon atoms, which alkyl group is partially or fully substituted with fluorine or chlorine; and R is an alkyl group having 1 to 6 carbon atoms, which alkyl group is partially or fully substituted with fluorine or chlorine comprising reacting a fluoroolefin of the formula RCX=CYZ with HF in the liquid-phase, in the presence of a catalytic effective amount of $SbF_5$.

The terms "alkyl group is partially or fully substituted with chlorine" and "chlorinated alkyl" are synonymous and it is meant that the alkyl group must be at least monosubstituted with Cl. Similarly, the terms "alkyl group is partially or fully substituted with fluorine" and "fluorinated alkyl" are synonymous and it is meant that the alkyl group must be at least monosubstituted with F. However, in both cases, the alkyl group may have one or more fluoro substituents thereon or one or more chloro substituents thereon or a combination of one or more chloro or fluoro groups thereon. Some of the carbon atoms may be substituted with one or more chloro or fluoro atoms. In an embodiment, the alkyl group is substituted with one or more fluoro atoms. In an embodiment, the alkyl group is fully substituted with chloro or fluoro or combination of both chloro and fluoro.

In another embodiment, the alkyl group is perchlorinated, while in another embodiment, the alkyl group is perfluorinated.

The alkyl group may be branched or linear. In an embodiment, the alkyl group is linear. In an embodiment, the alkyl group contains 1-4 carbon atoms, and in another embodiment, it contains 1 or 2 or 3 carbon atoms and in still another embodiment 1 or 2 carbon atoms. In another embodiment, it contains only 1 carbon atom. Examples include methyl, ethyl, n-propyl, isopropyl, n-butyl, isobutyl, sec-butyl and tert-butyl.

As defined herein, the carbon atoms which are part of the carbon-carbon double bond are substituted with R, X, Y, and Z. R is defined, among other things, as being partially or fully substituted with chloro or fluoro and X, Y, or Z may be, among other things, partially or fully substituted with chloro or fluoro. In one embodiment, X, Y, Z are independently partially or fully substituted with chloro or fluoro, and in another embodiment, two of X, Y, and Z are partially or fully substituted with chloro or fluoro, and in another embodiment, one of X, Y, and Z is partially or fully substituted with chloro or fluoro, in still another embodiment, three of X, Y and Z are partially or fully substituted with chloro or fluoro, and in another embodiment, none of X, Y, Z are partially or fully substituted with chloro or fluoro. With respect to X, Y, and Z, when defined as partially or fully substituted with chloro or fluoro, and with respect to R, in an embodiment, at least one carbon atom alpha or beta to the carbon atom bearing the double bond (if alkyl group contains 2 or more carbon atoms) is substituted with chloro or fluoro.

In one embodiment, X, Y, and Z are independently H or fluoro or chloro. In another embodiment, R is perchlorinated or perfluorinated. In some embodiments of this invention, R is $—CF_3$ or $—CF_2CF_3$. In another embodiment, X, Y, and Z are independently H or fluoro or chloro and R is perfluorinated or perchlorinated. In still further embodiment, X, Y, Z are independently H or fluoro or chloro and R is perfluorinated, for example, $—CF_3$ or $—CF_2CF_3$.

The process according to the invention can be carried out in any reactor made of a material that is resistant to reactants employed, especially to hydrogen fluoride. As used herein, the term "reactor" refers to any vessel in which the reaction may be performed in either a batchwise mode, or in a continuous mode. Suitable reactors include tank reactor vessels with and without agitators, or tubular reactors.

In one embodiment, the reactor is comprised of materials which are resistant to corrosion including stainless steel, Hastelloy, Inconel, Monel, gold or gold-lined or quartz. In another embodiment, the reactor is TFE or PFA-lined.

The olefin described herein has the formula RCX=CYZ, where R, X, Y, Z are as defined hereinabove. Examples include $RCCl=CH_2$, $RCH=CHCl$, $RCCl=CHCl$, $RCH=CCl_2$ and $RCH=CH_2$, and the like. In one embodiment, R is trifluoromethyl and in another embodiment, R is pentafluoroethyl. Representative olefins include 2-chloro-3, 3,3-trifluoropropene (HCFO-1233xf), 1-chloro-3,3,3-trifluoropropene (HCFO-1233zd), chlorotetrafluoropropenes (HCFO-1224 or 1224), 2,3,3,3-tetrafluoropropene (1234yf), dichlorotetrafluoropropenes (HCFO-1214 or 1214), 1,3,3,3- tetrafluoropropene (1234ze), 3,3,3-trifluoropropene (HFO-1243zf or 1234zf), and the like.

The hydrofluoroalkanes described herein are the addition products of HF to the fluoroolefins, as defined hereinabove. As defined herein, they have the formula RCXFCHYZ or RCXHCFYZ, wherein R, X, Y, Z are as defined hereinabove. As described hereinabove, in one embodiment, R is trifluoromethyl and in another embodiment, R is pentafluoroethyl.

Representative hydrofluoropropanes include 1,1,1,2-tetrafluoro-2-chloropropane, 1,1,1,3-tetrafluoro-3-chloropropane, 1,1,1,3,3-pentafluoro-3-chloropropane, 1,1,1,2,2-pentafluoro-3-chloropropane, 1,1,1,2,2-pentafluoropropane, 1,1,1,3,3-pentafluoropropane and the like.

The present process adds HF across the double bond of the fluoroolefin to produce a hydrofluoroalkane. The F atom may add to an internal or terminal carbon atom and the hydrogen atom may add to a terminal or internal carbon atom. Thus, for example, in accordance with the present disclosure, when the fluoroolefin is $RCCl=CH_2$, the product is $RCFClCH_3$. In another embodiment, when the fluoroolefin is $RCH=CHCl$, the product is $RCH_2CHFCl$. In another embodiment, when the fluoroolefin is $RCH=CCl_2$, the hydrofluoropropane is $RCH_2CFCl_2$. In yet another embodiment, when the fluoroolefin is $RCH=CH_2$, the hydrofluoropropanes formed are $RCHFCH_3$ and $RCH_2CH_2F$. With respect to the aforementioned examples, in an embodiment, R can be $CF_3$ or $C_2F_6$.

In one embodiment, the fluoroolefin is 2-chloro-3,3,3-trifluoropropene and the hydrofluoroalkane is 2-chloro-1,1,1,2-tetrafluoropropane. In another embodiment, the fluoroolefin is 3,3,3-trifluoropropene and the hydrofluoroalkane is 1,1,1,2-tetrafluoropropane and 1,1,1,3-tetrafluoropropane. In another embodiment, the fluoroolefin is (Z)- or (E)-1-chloro-3,3,3-tetrafluoropropene and the hydrofluoroalkane is 3-chloro-1,1,1,3-tetrafluoropropane. In another embodiment, the fluoroolefin is cis- or trans-1,2-dichloro-3,3,3-trifluoropropene and the hydrofluoroalkane is 1,1,1,2-tetrafluoro-2,3-dichloropropane and 1,1,1,3-tetrafluoro-2,3-dichloropropane. In another embodiment, the fluoroolefin is 2,3,3,3-tetrafluoropropene, and the hydrofluoroalkane is 1,1,1,2,2,2-pentafluoropropane. In yet another embodiment, the fluoroolefin is 1,3,3,3-tetrafluoropropene and the hydrofluoroalkane is 1,1,1,3-pentafluoropropane.

Without wishing to be bound, it is believed that with respect to HF addition to a carbon-carbon double bond, the fluorine atom adds to the carbon atom of the double bond which has the most halogens attached thereto. Otherwise, without wishing to be bound, the HF is added to the carbon atom of the double bond in accordance with Markovnikov's rule, i.e., the hydrogen of HF will add to the carbon atom that will form the more stable carbonium ion. Thus, for example, if one of the carbon atoms of the carbon-carbon double bond has more hydrogen atoms substituted thereon than the other carbon atom of the carbon-carbon double bond, the hydrogen atom of HF will add to the carbon atom having the most hydrogen atoms substituted thereon.

The above process is conducted in the liquid phase. The fluoroolefin as well as the hydrogen fluoride are liquids at reaction conditions. Since water is used to quench the reaction, the amount of water present is minimized. For example, the hydrogen fluoride used is anhydrous.

The hydrogen fluoride can be bubbled in as a gas or added as a liquid into the liquid fluoroolefin or it may be present in an anhydrous solvent, such as pyridine. Thus, for example, in an embodiment, although not necessary, the fluoroolefin is dried with a desiccant before being mixed with HF or the catalyst. By "desiccant," it is meant any material which will absorb water without dissolving in or otherwise contaminating the fluoroolefin being dried, e.g., calcium sulfate or molecular sieves, and the like. In another embodiment, the reaction can be conducted in an inert atmosphere, such as under nitrogen, helium, argon and the like. However, in an embodiment, the reaction can be conducted in air and in another embodiment, the reaction is conducted without drying the fluoroolefin.

In an embodiment, when anhydrous liquid HF is used or HF is fed as a gas, the reaction is conducted without any solvent in addition to the solvent in which the anhydrous HF is dissolved.

If the HF is fed as a gas, such as, being bubbled in as a gas, the reaction may be conducted without any solvent present.

In one embodiment, the hydrofluorination reaction is conducted at a temperature ranging from about −30° C. to about 65° C. In another embodiment, the hydrofluorination reaction is conducted at a temperature ranging from about −10° C. to about 40° C. In another embodiment, the hydrofluorination reaction is conducted at a temperature ranging from about 0° C. to about 30° C.

In still another embodiment, the hydrofluorination reaction is conducted at a temperature ranging from about 0° C. to about 25° C. In another embodiment, the hydrofluorination reaction is conducted at a temperature ranging from about 5° C. to about 25° C. In still another embodiment, the hydrofluorination reaction is conducted at a temperature ranging from about 5° C. to about 20° C. Moreover, the hydrofluorination reaction can be conducted at any temperature in-between the ranges disclosed hereinabove, and these temperatures are contemplated within the scope of the present invention. Thus, the hydrofluorination described hereinabove is conducted in a reaction vessel at about −30° C., about −29° C., about −28° C., about −27° C., about −26° C., about −25° C., about −24° C., about −23° C., about −22° C., about −21° C., about −20° C., about −19° C., about −18° C., about −17° C., about −16° C., about −15° C., about −14° C., about −13° C., about −12° C., about −11° C., about −10° C., about −9° C., about −8° C., about −7° C., about −6° C., about −5° C., about −4° C., about −3° C., about −2° C., about −1° C., about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., or about 65° C.

In an embodiment, the reaction mixture is stirred using techniques known in the art. For example, the reaction mixture is spun using a stirring bar. Alternatively, the reactor in which the reaction takes place is equipped with an impeller or other stirring device which stirs the reaction mixture.

In another embodiment, mixing may be provided by alternatives to stirring devices. Such methods are known in the industry and include using the mixing provided by gas bubbles from gas added to the vessel or generated within the vessel by vaporization of liquid. Mixing can also be provided by withdrawing the liquid from the vessel to a pump and pumping the liquid back into the vessel. A static mixer or other device intended to mix the contents can be present in the circulation path of the liquid to provide additional mixing power input.

In one embodiment, the mole ratio of HF to fluoroolefin ranges from about 0.5 to about 20.

In another embodiment, the mole ratio of HF to fluoroolefin is from about 1 to about 10. In another embodiment, the mole ratio of HF to fluoroolefin is from about 1 to about 5.

The SbF5 is present in catalytic effective amounts. In one embodiment, the SbF5 catalyst is present from about 1% to about 50% by weight of the mixture. In another embodiment, the SbF5 catalyst is present from about 2% to about 30% by weight. In another embodiment, the SbF5 catalyst is present from about 3% to about 15% by weight.

As described hereinabove, hydrofluoroalkanes are prepared by catalytic fluorination of the fluoroolefin. In one embodiment, the catalytic fluorination of the fluoroolefin results in a percent conversion to the hydrofluoroalkane of at least 90 mole %. In another embodiment, the catalytic fluorination of the fluoroolefin results in a percent conversion to the hydrofluoroalkane of at least 95%. In another embodiment, the catalytic fluorination of the fluoroolefin results in a percent conversion to the hydrofluoroalkane of at least 98%. In still another embodiment, the catalytic fluorination of the fluoroolefin results in a percent conversion to the hydrofluoroalkane of at least 99%.

An aspect of the invention is to replace step (ii) of the reaction for making 1234yf described in the introduction with the present process.

One of the advantages of the present disclosure is that the catalytic reaction for hydrofluorination, as described herein, takes place at lower temperatures, much lower than other catalysts for the other hydrofluorination reactions of fluoroolefin, such as SbCl5 or fluorinated SbCl5. Unlike these other catalysts, SbF5 is a liquid at these lower temperatures that are used in the present process. Therefore, less energy is required to conduct these hydrofluorination reactions.

In addition, in the present process, the catalyst has substantial activity at the lower temperature.

Thus, the catalytic process proceeds at a low temperature, thereby making it more efficient.

In addition, another advantage is that the ratio of the desired hydrofluoroalkane produced relative to the starting olefin is about 90:1 or greater, and in another embodiment, is about 100:1 or greater and in another embodiment is about 110:1 or greater. Thus, for another reason, this reaction is quite efficient.

Moreover, in view of the efficiency, if an olefin and the resulting hydrofluoroalkane from the hydrofluorination reaction, such as 1233xf and 244bb, were mixed together and reacted under the conditions of the present invention with SbF5, additional hydrofluoroalkane product would be formed. For example, in one embodiment, if the feed material ratio of olefin, such as 1233xf, to hydrofluoroalkane, such a 244bb, is greater than about 1 mole %, the present process will significantly convert the unreacted olefin to hydrofluoroalkane, thereby increasing the amount of the hydrofluoroalkane in the mixture. The present disclosure thus provides a method of maximizing the yield of the desired hydrofluoroalkane relative to the olefin. Thus, in the above example, wherein the olefin is 1233xf and the hydrofluoroalkane is 244bb, if 1233xf is present in greater than about 1 mole %, the resulting product would have significantly more 244bb present than prior to the reaction.

Thus, in one embodiment, this advantage of the present disclosure can be used to improve the yield of HFO-1234yf being produced. As described hereinabove, the preparation of HFO-1234yf may include at least three reaction steps, as follows:

(i) ($CQ_2=CCl-CH_2Q$ or $CQ_3-CCl=CH_2$ or $CQ_3$-$CHCl-CH_2Q$)+$HF$-2-chloro-3,3,3- trifluoropropene (HCFO-1233xf)+HCl in a vapor phase reactor charged with a solid catalyst;

(ii)2-chloro-3,3,3-trifluoropropene(HCFO-1233x$f$)+ $HF$→2-chloro-1,1,1,2

-tetrafluoropropane (HCFC-244bb) in a liquid phase reactor charged with a liquid hydrofluorination catalyst; and (iii) 2-chloro-1,1,1,2-tetrafluoropropane (HCFC-244bb)-2,3,3,3-tetrafluoropropene (HFO-1234yf) in a vapor phase reactor.

The general reactions of steps (i), (ii) and (iii) are well known in the art. For example, they are described in U.S. Pat. No. 8,846,990, the contents of which are incorporated by reference.

In the first step, a starting composition, which comprises 1,1,2,3-tetrachloropropene (HCO-1230xa or 1230xa), reacts with anhydrous HF in a first reactor (fluorination reactor) to produce a mixture of at least HCFO-1233xf (2-chloro-3,3,3-trifluoropropene) and HCl. The reaction is carried out in a reactor in the gaseous phase at a temperature of about 200° C. to about 400° C. and a pressure of about 0 to about 200 psig. The effluent stream exiting in the vapor phase reactor may optionally comprise additional components, such as un-reacted HF, un-reacted starting composition, heavy intermediates, HFC-245cb, or the like.

This reaction may be conducted in any reactor suitable for a vapor phase fluorination reaction. The reactor may be constructed from materials which are resistant to the corrosive effects of hydrogen fluoride such as Hastelloy, Inconel, Monel, and the like. In the case of a vapor phase process, the reactor is filled with a vapor phase fluorination catalyst. Any fluorination catalysts known in the art may be used in this process. Suitable catalysts include, but are not limited to, metal oxides, hydroxides, halides, oxyhalides, inorganic salts thereof and their mixtures, any of which may be optionally halogenated, wherein the metal includes, but is not limited to, chromium, aluminum, cobalt, manganese, nickel, iron, and combinations of two or more thereof.

Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082, the contents of which are incorporated herein by reference. Chromium (III) oxides such as crystalline chromium oxide or amorphous chromium oxide are preferred with amorphous chromium oxide being most preferred. Chromium oxide ($Cr_2O3$) is a commercially available material which may be purchased in a variety of particle sizes. Fluorination catalysts having a purity of at least 98% are preferred. The fluorination catalyst is present in an excess but in at least an amount sufficient to drive the reaction.

This first step of the reaction is not necessarily limited to a vapor phase reaction and may also be performed using a liquid phase reaction or a combination of liquid and vapor phases, such as that disclosed in U.S. Published Patent Application No. 2007/0197842, the contents of which are incorporated herein by reference. It is also contemplated that the reaction can be carried out batch wise or in a continuous manner, or a combination of these.

For embodiments in which the reaction comprises a liquid phase reaction, the reaction can be catalytic or non-catalytic. Lewis acid catalysts, such as metal-halide catalysts, including antimony halides, tin halides, thallium halides, iron halides, and combinations of two or more of these, may be employed. In certain embodiments, metal chlorides and metal fluorides are employed, including, but not limited to, $SbCl_5$, $SbCl_3$, $SbF_5$, $SnCl_4$, $TiCl_4$, $FeCl_3$, and combinations of two or more of these. It is noted that $SbF_5$ is a liquid at low temperature.

In the second step of the process for forming 2,3,3,3-tetrafluoropropene, HCFO-1233xf is converted to HCFC-244bb. In one embodiment, this step can be performed in the liquid phase in a liquid phase reactor, which may be TFE or PFA-lined. Such a process can be performed in a temperature range of about 70° C. to about 120° C. and at a pressure ranging from about 50 to about 120 psig. Any liquid phase fluorination catalyst may be used that is effective at these temperatures.

A non-exhaustive list includes Lewis acids, transition metal halides, transition metal oxides, Group IVb metal halides, Group Vb metal halides, or combinations thereof. Non-exclusive examples of liquid phase fluorination catalysts are antimony halide, tin halide, tantalum halide, titanium halide, niobium halide, molybdenum halide, iron halide, fluorinated chrome halide, fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_1$, $FeCl_3$, fluorinated species of $SbCl_5$, fluorinated species of $SbCl_3$, fluorinated species of $SnCl_4$, fluorinated species of $TaCl_5$, fluorinated species of $TiCl_4$, fluorinated species of $NbCl_5$, fluorinated species of $MoCl6$, fluorinated species of $FeCl_3$, or combinations thereof.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 2007/0197842, the contents of which are incorporated herein by reference. To this end, the HCFO-1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the process described in the art, such as that described in U.S. Published Patent Application No. 2007/0197842, the product from the second step is then transferred to a third reactor wherein the 244bb is dehydrohalogenated. The catalysts in the dehydrochlorination reaction may be or comprise metal halide, halogenated metal oxide, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals of metal halides, oxides and their mixtures/combinations include, but are not limited to, $Cr^{3+}$, $Fe^{3+}$, $Mg^{2+}$, $Ca^{2+}$, Ni2+, $Zn^{2+}$, $Pd^{2+}$, Li+, Na+, K+, and Cs+. Component halides include, but are not limited to, F, Cl, Br, and I. Examples of useful mono- or bi-valent metal halide include, but are not limited to, LiF, NaF, KF, CsF, $MgF_2$, $CaF_2$, LiCi, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When the catalyst is or comprises a neutral, i.e., zero valent metal, then metals and metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625. Such catalysts may be provided as discrete supported or unsupported elements and/or as part of the reactor and/or the reactor walls.

Preferred, but non-limiting, catalysts include activated carbon, stainless steel (e.g., SS 316), austenitic nickel-based alloys (e.g., Inconel 625), nickel, fluorinated 10% CsCl/MgO, and 10% $CsCl/MgF_2$. A suitable reaction temperature is about 300° C. to about 550° C. and a suitable reaction pressure may be between about 0 psig to about 150 psig. The reactor effluent may be fed to a caustic scrubber or to a distillation column to remove the byproduct of HCl to produce an acid-free organic product which, optionally, may undergo further purification using one or any combination of purification techniques that are known in the art.

The dehydrohalogenation reaction is carried out in the vapor phase. It may be carried out at a temperature range of from about 200° C. to about 800° C., from about 300° C. to about 600° C., or from about 400° C. to about 500° C. Suitable reactor pressures range from about 0 psig to about 200 psig, from about 10 psig to about 100 psig, or from about 20 to about 70 psig.

A method of increasing the yield and conversion of 1233xf to 1234yf and to make the process more efficient is to react the product of step (ii), which contains a mixture of 1233xf and 244bb, with $SbF_5$ in accordance with the process of the present invention prior to the dehydrochlorination step. This increases the amount of 244bb present (decreasing the amount of 1233xf present) and the resulting product can then be subjected to step (iii) above. By conducting this additional hydrofluorination reaction, more 244bb is produced, and as a result, significantly more 1234yf is produced. The 244bb thus produced is then transferred to another reactor wherein it undergoes dehydrohalogenation, in accordance with step (iii).

Alternatively, as described above, instead of conducting step (ii) of the process, the 1233xf produced in step (i) is hydrofluorinated with HF in the presence of $SbF_5$, in accordance with the present invention, as described herein. The 244bb product thus formed is then dehydrochlorinated to form 1234yf, in accordance with step (iii) described hereinabove.

The following non-limiting examples further illustrate the invention.

Examples

Example 1-1233xf Hydrofluorination by HF with $SbF_5$ Catalyst at 30 C 13.8 g of HF and 5 g of $SbF_5$ were loaded into a 210 mL shaker tube reactor. The reactor was then evacuated and chilled to −15° C. 30 g of 1233xf was added into the reactor. The reactor was then heated to 30° C. with agitation. Once the temperature reached 30° C., water was added to the reactor to quench the catalyst. The organic layer was vapor transferred into a stainless steel cylinder and analyzed by GC-MS. Table 1 below shows the results of the GC-MS analysis.

TABLE 1

|  | mol % | mol ratio 1233xf/244bb |
|---|---|---|
| 143a | 0.005% |  |
| 245cb | 0.032% |  |
| 245fa | 0.059% |  |
| Unknown | 0.001% |  |
| 244bb | 99.420% | 0.48% |
| 1233xf | 0.474% |  |
| 243ab | 0.009% |  |

Example 2-1233xf Hydrofluorination by HF with SbF$_5$ Catalyst at 10 C 13.8 g of HF and 5 g of SbF$_5$ were loaded into a 210 mL shaker tube reactor. The reactor was then evacuated and chilled to −15° C. 30 g of 1233xf was added into the reactor. The reactor was then heated to 10° C. with agitation. Once the temperature reached 10° C., water was added to the reactor to quench the catalyst. The organic layer was vapor transferred into a stainless steel cylinder and analyzed by GC-MS. Table 2 below shows the results of the GC-MS analysis.

TABLE 2

| Compounds | mol % | mol ratio 1233xf/244bb |
|---|---|---|
| 245cb | 0.017% |  |
| 245fa | 0.0200% |  |
| 244bb | 98.236% |  |
| 1233xf | 0.794% | 0.81% |
| 1233xf dimer | 0.934% |  |

Examdle 3-m233xfHydrofluorination by HF with SbF$_5$ Catalyst at 30/4

10.00g of HBF and 5 g of SbF$_S$ were loaded into a 210 mL shaker tube reactor. The reactor was then evacuated and chilled to −40 C. 308 g of 1233xf was added into the reactor. The reactor was then heated to 30° C. with agitation and stirred for an hour. The reactor was chilled to −30° C. quickly and 75 mL of water was added to the reactor to quench the catalyst. The organic layer was vapor transferred into a stainless steel cylinder and analyzed by GC-MS. Table 3 below shows the results of the GC-MS analysis.

TABLE 3

| Compound | mol % | mol ratio 1233xf/244bb |
|---|---|---|
| 245cb | 14.412% |  |
| 245fa | 0.096% |  |
| 244bb | 84.147% |  |
| 1233xf | 0.768% | 0.91% |
| 243ab | 0.576% |  |

Comparative Example 1-1233xf-244bb Equilibrium by HF with Fluorination SbCl$_5$ Catalyst at 80° C.

18.0 g of HF and 14.0 g of SbCl$_5$ were loaded into a 210 mL shaker tube reactor and heated at 100° C. for 2 hours with agitation. The reactor was then evacuated and chilled to 0° C. to vent off HCl. 20 g of 244bb (99.7 mol %) was added into the reactor. The reactor was then heated to 80° C. for an hour and then quickly chilled to 30° C. Water was added to the reactor to quench the catalyst. The organic layer was vapor transferred into a stainless steel cylinder and analyzed by GC-MS. Table 4 below shows the results of the GC-MS analysis. The 1233xf/244bb ratio increased to 1.95 mol % from 0.3 mol %. This indicates the existence of equilibrium between 1233xf and 244bb which prevents the full conversion of 1233xf to 244bb.

TABLE 4

|  | mol % | mol ratio 1233xf/244bb |
|---|---|---|
| 245cb | 0.089% |  |
| 244bb | 92.907% |  |
| 1233xf | 1.815% | 1.95% |
| 243ab | 4.905% |  |
| Others | 0.284% |  |

Many aspects and embodiments have been described and are merely exemplary and not limiting. After reading the specification, skilled artisans appreciate that other aspects and embodiments are possible without departing from the scope of the invention.

Other features and benefits of any one or more of the embodiments will be apparent from the hereinabove detailed description and the claims.

What is claimed is:
1. A composition comprising:
   a mixture comprising HF, SbF$_5$, olefin, and a hydrofluoroalkane;
   wherein the olefin and the hydrofluoroalkane are selected from:
   a) the olefin is (Z)-1-chloro-3,3,3-trifluoropropene or (E)-1-chloro-3,3,3-trifluoropropene and the hydrofluoroalkane is 3-chloro-1,1,13-tetrafluoropropane;
   b) the olefin is 1-chloro-2,3,3,3-tetrafluoropropene and the hydrofluoroalkane is 1,1,1,2,2-pentafluoro-3-chloropropane and 1,1,1,2,3-pentafluoro-3-chloropropane;
   c) the olefin is 2,3,3,3-tetrafluoropropene and the hydrofluoroalkane is 1,1,1,2,2-pentafluoropropane; and
   d) the olefin is 1,3,3,3-tetrafluoropropene and the hydrofluoroalkane is 1,1,1,3,3-pentafluoropropane; and
   wherein the SbF$_5$ is present in an amount in the range of about 2% to about 30%, by weight of the mixture.
2. The composition of claim 1, wherein the SbF$_5$ is present in an amount in the range of about 3% to about 15%, by weight of the mixture.
3. The composition of claim 2, wherein the SbF$_5$ is present in an amount in the range of about 10% to about 11%, by weight of the mixture.
4. The composition of claim 3, wherein the composition is a liquid.
5. The composition of claim 1, wherein the mole ratio of HF to the olefin is in the range of from 1 to 10.
6. The composition of claim 5, wherein the mole ratio of HF to the olefin is in the range of from 1 to 5.

7. The composition of claim 1, wherein the olefin is (Z)-1-chloro-33,3-trifluoropropene or (E)-1-chloro-3,3,3-trifluoropropene and the hydrofluoroalkane is 3-chloro-1,1,1,3-tetrafluoropropane.

8. The composition of claim 1, wherein the olefin is 1-chloro-2,3,3,3-tetrafluoropropene and the hydrofluoroalkane is 1,1,1,2,2-pentafluoro-3-chloropropane and 1,1,1,2,3-pentafluoro-3-chloropropane.

9. The composition of claim 1, wherein the olefin is 2,3,3,3-tetrafluoropropene and the hydrofluoroalkane is 1,1,1,2,2-pentafluoropropane.

10. The composition of claim 1, wherein the olefin is 1,3,3,3-tetrafluoropropene and the hydrofluoroalkane is 1,1,1,3,3-pentafluoropropane.

11. The composition of claim 7, wherein the olefin is (Z)-1-chloro-3,3,3-trifluoropropene.

12. The composition of claim 7, wherein the olefin is (E)-1-chloro-3,3,3-trifluoropropene.

13. The composition of claim 7, wherein the $SbF_5$ is present in an amount in the range of about 3% to about 15%, by weight of the mixture.

14. The composition of claim 13, wherein the $SbF_5$ is present in an amount in the range of about 10% to about 11%, by weight of the mixture.

15. The composition of claim 8, wherein the $SbF_5$ is present in an amount in the range of about 3% to about 15%, by weight of the mixture.

16. The composition of claim 15, wherein the $SbF_5$ is present in an amount in the range of about 10% to about 11%, by weight of the mixture.

17. The composition of claim 9, wherein the $SbF_5$ is present in an amount in the range of about 3% to about 15%, by weight of the mixture.

18. The composition of claim 17, wherein the $SbF_5$ is present in an amount in the range of about 10% to about 11%, by weight of the mixture.

19. The composition of claim 10, wherein the $SbF_5$ is present in an amount in the range of about 3% to about 15%, by weight of the mixture.

20. The composition of claim 19, wherein the $SbF_5$ is present in an amount in the range of about 10% to about 11%, by weight of the mixture.

* * * * *